United States Patent
Tseng et al.

(10) Patent No.: US 6,733,524 B2
(45) Date of Patent: *May 11, 2004

(54) POLYMER COATED STENT

(75) Inventors: David Tseng, Cambridge, MA (US); William Donahue, Chester, NJ (US); Bruce A. Parsons, Oakland Park, FL (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/067,584

(22) Filed: Feb. 5, 2002

(65) Prior Publication Data

US 2002/0091437 A1 Jul. 11, 2002

Related U.S. Application Data

(63) Continuation of application No. 09/272,538, filed on Mar. 19, 1999, now Pat. No. 6,364,903.

(51) Int. Cl.[7] ................................................. A61F 2/06
(52) U.S. Cl. .................... 623/1.46; 427/2.24; 623/1.15
(58) Field of Search ............................... 623/1.46, 1.22, 623/1.13, 1.5–1.54; 427/2.1–2.31

(56) References Cited

U.S. PATENT DOCUMENTS

| | | | |
|---|---|---|---|
| 4,925,710 A | 5/1990 | Buck | |
| 5,123,917 A | 6/1992 | Lee | |
| 5,282,824 A | 2/1994 | Gianturco | |
| 5,389,106 A | 2/1995 | Tower | |
| 5,443,497 A | * 8/1995 | Venbrux | .................... 623/1.13 |
| 5,466,509 A | 11/1995 | Kowligi et al. | |
| 5,507,771 A | 4/1996 | Gianturco | |
| 5,554,181 A | * 9/1996 | Das | .................... 623/1.12 |
| 5,562,697 A | 10/1996 | Christiansen | |
| 5,562,728 A | 10/1996 | Lazarus et al. | |
| 5,590,639 A | 1/1997 | Kempin | |
| 5,591,195 A | 1/1997 | Taheri et al. | |
| 5,620,763 A | 4/1997 | House et al. | |
| 5,653,697 A | 8/1997 | Quiachon et al. | |
| 5,674,241 A | 10/1997 | Bley et al. | |
| 5,700,285 A | 12/1997 | Myers et al. | |
| 5,713,917 A | 2/1998 | Leonhardt et al. | |
| 5,718,973 A | 2/1998 | Lewis et al. | |
| 5,735,892 A | 4/1998 | Myers et al. | |
| 5,749,880 A | 5/1998 | Banas | |
| 5,788,626 A | 8/1998 | Thompson | |
| 5,800,512 A | 9/1998 | Lentz et al. | |
| 5,824,037 A | 10/1998 | Fogarty et al. | |
| 5,843,172 A | * 12/1998 | Yan | .................... 623/1.42 |
| 5,851,232 A | 12/1998 | Lois | |
| 5,858,556 A | 1/1999 | Eckert et al. | |
| 5,888,591 A | 3/1999 | Gleason et al. | |

(List continued on next page.)

FOREIGN PATENT DOCUMENTS

| | | |
|---|---|---|
| EP | 0 855 170 | 7/1998 |
| WO | WO 95/05132 | 2/1995 |
| WO | WO 95/05555 | 2/1995 |
| WO | WO 96/28115 | 9/1996 |
| WO | WO 98/00090 | 1/1998 |
| WO | WO 98/12990 | 4/1998 |
| WO | WO 98/38947 | 9/1998 |

Primary Examiner—David H. Willse
Assistant Examiner—Suzette J. Jackson
(74) Attorney, Agent, or Firm—Hoffmann & Baron, LLP

(57) ABSTRACT

A tubular intraluminal prosthesis includes a PTFE or ePTFE tubular structure such as a graft, and a tubular diametrically deformable stent circumferentially surrounding the tubular structure. The diametrically deformable stent includes a polymeric coating which allows for attachment to the tubular graft structure and enhances the biocompatibility and integrity of the composite prosthesis.

14 Claims, 7 Drawing Sheets

U.S. PATENT DOCUMENTS

| | | |
|---|---|---|
| 5,891,507 A | 4/1999 | Jayaraman |
| 5,895,407 A | 4/1999 | Jayaraman |
| 5,906,639 A * | 5/1999 | Rudnick et al. ............ 623/1.15 |
| 5,922,393 A | 7/1999 | Jayaraman |
| 5,925,075 A | 7/1999 | Myers et al. |
| 5,928,279 A * | 7/1999 | Shannon et al. ........... 623/1.13 |
| 6,053,943 A * | 4/2000 | Edwin et al. .............. 623/1.25 |
| 6,129,757 A * | 10/2000 | Weadock ................... 623/1.39 |
| 6,139,573 A * | 10/2000 | Sogard et al. ............. 623/1.13 |
| 6,245,099 B1 * | 6/2001 | Edwin et al. .............. 623/1.13 |
| 6,264,684 B1 * | 7/2001 | Banas et al. ............... 623/1.13 |
| 6,364,903 B2 * | 4/2002 | Tseng et al. ............... 623/1.15 |
| 6,447,542 B1 * | 9/2002 | Weadock ................. 623/11.11 |
| 6,488,701 B1 * | 12/2002 | Nolting et al. ............. 623/1.13 |

\* cited by examiner

POLYMER COATED STENT

This is a continuation of application Ser. No. 09/272,538, filed Mar. 19, 1999. Now U.S. Pat. No. 6,364,903.

FIELD OF INVENTION

The present invention relates generally to a tubular implantable prosthesis formed of porous polytetrafluoroethylene. More particularly, the present invention relates to a stent/graft composite device including a polymeric coated stent in conjunction with an ePTFE graft.

BACKGROUND OF RELATED TECHNOLOGY

An endoluminal prosthesis is a medical device commonly known to be used in the treatment of diseased blood vessels. An endoluminal prosthesis is typically used to repair, replace, or otherwise correct a damaged blood vessel. An artery or vein may be diseased in a variety of different ways. The prosthesis may therefore be used to prevent or treat a wide variety of defects such as stenosis of the vessel, thrombosis, occlusion, or an aneurysm.

One type of endoluminal prosthesis used in the repair of diseases in various body vessels is a stent. A stent is a generally longitudinal tubular device which is useful to open and support various lumens in the body. For example, stents may be used in the vascular system, urogenital tract and bile duct, as well as in a variety of other applications in the body. Endovascular stents have become widely used for the treatment of stenosis, strictures, and aneurysms in various blood vessels. These devices are implanted within the vessel to open and/or reinforce collapsing or partially occluded sections of the vessel.

Stents are generally open ended and are radially expandable between a generally unexpanded insertion diameter and an expanded implantation diameter which is greater than the unexpanded insertion diameter. Stents are often flexible in configuration, which allows them to be inserted through and conform to tortuous pathways in the blood vessel. The stent is generally inserted in a radially compressed state and expanded either through a self-expanding mechanism, or through the use of balloon catheters.

A graft is another type of endoluminal prosthesis which is used to repair and replace various body vessels. Whereas a stent provides structural support to hold a damaged vessel open, a graft provides an artificial lumen through which blood may flow. Grafts are tubular devices which may be formed of a variety of material, including textile and non-textile materials. One type of non-textile material particularly suitable for use as an implantable prosthesis is polytetrafluoroethylene (PTFE). PTFE exhibits superior biocompatibility and low thrombogenicity, which makes it particularly useful as vascular graft material in the repair or replacement of blood vessels. In vascular applications, the grafts are manufactured from expanded PTFE (ePTFE) tubes. These tubes have a microporous structure which allows natural tissue ingrowth and cell endothelialization once implanted in the vascular system. This contributes to long term healing and patency of the graft.

It is also known to combine a stent and a graft to form a composite medical device. Such devices are often referred to as stent/grafts. Such a composite medical device provides additional support for blood flow through weakened sections of a blood vessel. In endovascular applications the use of a stent/graft combination is becoming increasingly important because the combination not only effectively allows the passage of blood therethrough, but also ensures the implant will remain open and stable. However, the graft can reduce the overall longitudinal flexibility of the composite device. Longitudinal flexibility is of particular importance to such stent/graft endoluminal prosthesis as the device must be intraluminally delivered through tortuous pathways of a blood vessel to the implantation site where the stent is expanded.

Several types of stent/graft inventions are known in the art. For example, U.S. Pat. No. 5,151,105 issued to Kwan-Gett discloses a collapsible textile vessel sleeve that is collapsible to a very small diameter in order that it may be placed in position within the abdominal or thoracic aorta by a catheter via the lumen of the femoral artery. Such a procedure obviates the need for a major surgical intervention, and reduces the risks associated with such a procedure. Other stent/graft composite devices using a fabric are shown in U.S. Pat. No. 5,628,788 to Pinchuck.

U.S. Pat. No. 5,575,818 issued to Pinchuk discloses polyurethane coatings which may be applied to a stent to form a stent/graft. The coatings disclosed may be bonded to the stent through the use of many different methods. For example, an inner lining or coating can be first spun on a mandrel, after which a stent covered with an adhesive substance is pulled down on the lining and then the adhesive is cured, melted and solidified or dried. Another alternative is to place the stent on a mandrel, apply (e.g., spray, dip, pad, etc.) a thin coating of polyurethane lacquer over the stent, and then spin the coating over the lacquer so that it is bonded to the stent once the lacquer dries.

One difficulty encountered in stent/graft structures which employ PTFE or ePTFE as the graft portion, is obtaining a proper bond between the stent, which is usually metallic or other material dissimilar to the graft portion. For example, U.S. Pat. Nos. 5,700,285, 5,735,892 and 5,810,870 to Myers et al. disclose the use of two ePTFE tubular sheets which are bonded together through the space between a stent sandwiched therebetween. These patents also disclose the use of fluorinated ethylene propylene (FEP) as an adhesive for bonding the stent to a tubular sheet or sheets.

It is well recognized, however, that few materials bond well to PTFE or ePTFE due to its chemical makeup. The surface of PTFE materials is difficult to wet and the relatively small pore sizes of ePTFE are difficult to penetrate effectively to obtain good mechanical bonds.

Thus, while ePTFE has shown to possess many desirous characteristics for use in conjunction with a stent, attachment of the polymeric tubular grafts to the stent has always presented its challenges. Due to the physical and chemical inertness of an ePTFE vascular graft, thus, it is difficult to adheringly attach such grafts to other structures. The present invention addresses inherent difficulty in bonding the stent.

SUMMARY OF THE INVENTION

It is therefore an advantage provided by the present invention to provide a composite stent/graft prosthesis exhibiting both the benefits of a composite endoluminal stent/graft prosthesis while maintaining the flexibility of an uncovered stent.

It is a further advantage provided by the present invention to provide a biocompatible surface to an uncovered stent through the application of a polymeric material coating which is capable of adhering to PTFE or ePTFE.

In the efficient attainment of these and other objects, the present invention provides a tubular intraluminal prosthesis including at least one PTFE tubular structure with opposed interior and exterior surfaces. A tubular diametrically deformable stent is at least partially coated with a polymeric coating, and the at least partially coated stent is affixed to said tubular structure at the portions of the stent. A second PTFE tubular structure on the remaining uncovered side of the stent is also contemplated.

A method of forming the intraluminal prosthesis is also provided, which includes the providing a tubular stent, coating at least a portion of said stent with a polymeric coating applied from a liquid or particulate state, providing a tubular PTFE graft structure, and affixing said coated stent to said tubular PTFE graft structure.

DETAILED DESCRIPTION OF THE INVENTION

The following is a detailed description of the preferred embodiments of the present invention. The description is meant to describe preferred embodiments, and is not meant to limit the invention in any way.

Various stent types and stent constructions may be employed in the invention. Among the various stents useful include, without limitation, self-expanding stents and balloon expandable extents. The stents may be capable of radially contracting, as well, and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents.

The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like.

Figure 1:
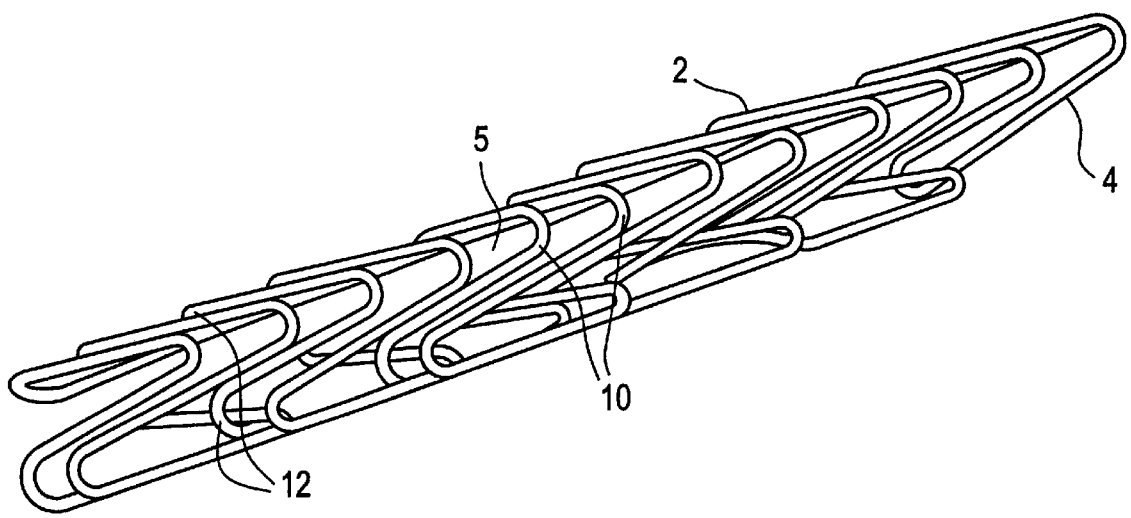
FIG. 1 is a perspective showing of a collapsed standard wave-like stent which may be used in the present intraluminal prosthesis.
Figure 4:
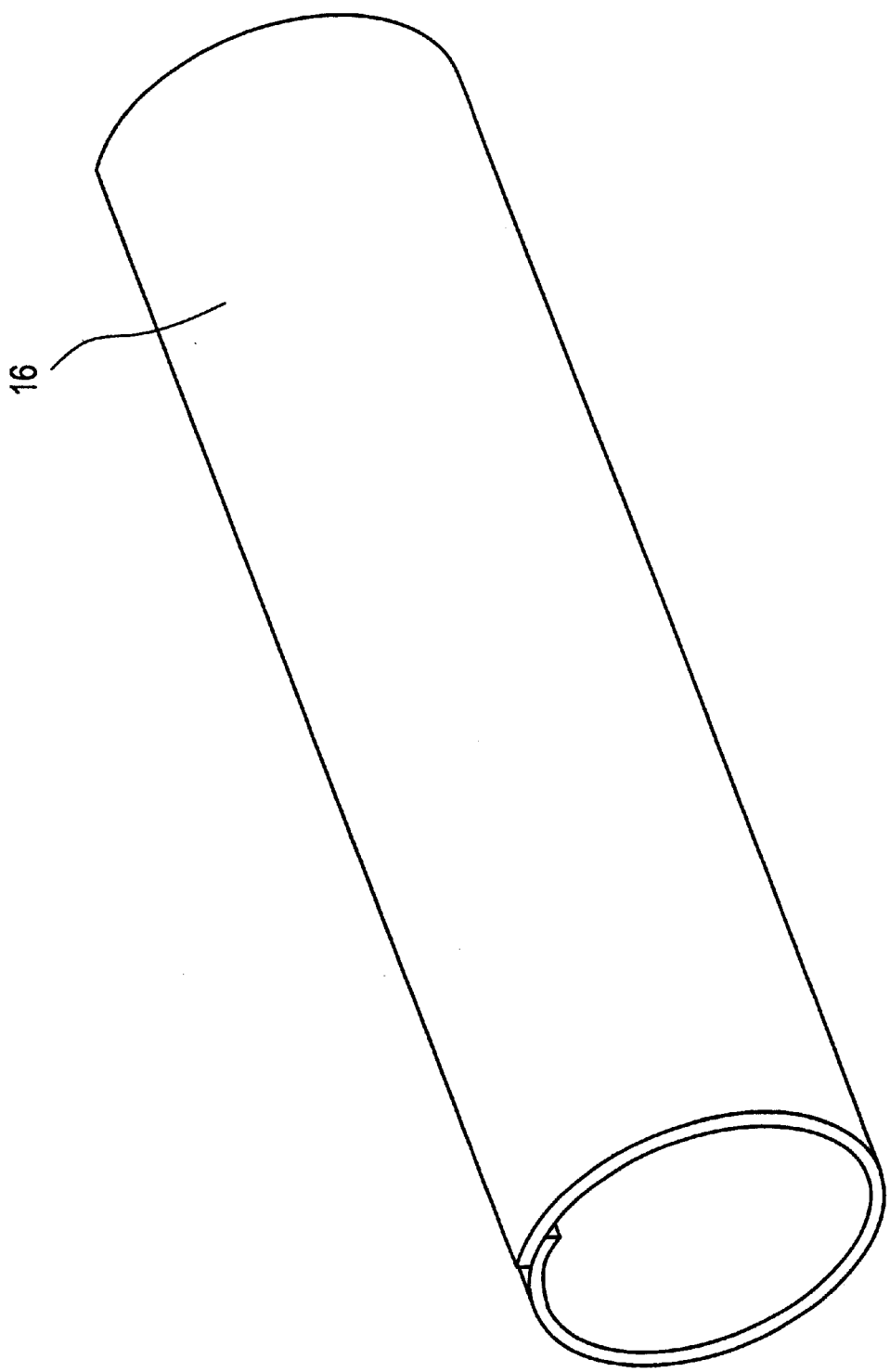
FIG. 4 is a perspective showing of an ePTFE tube formed from a wrapped sheet.
Figure 5:
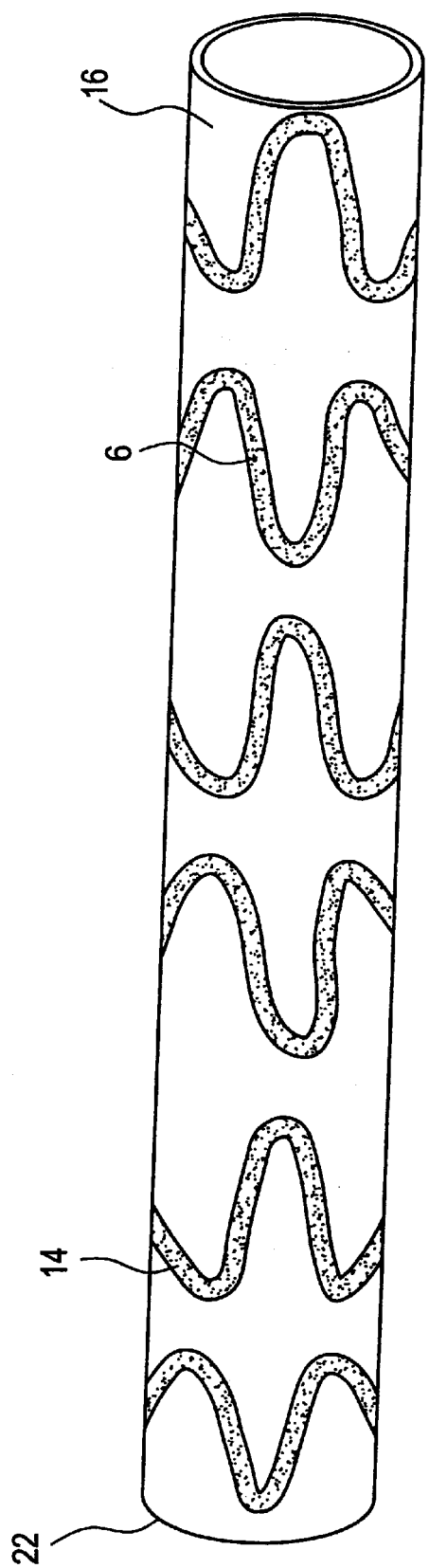
FIG. 5 is a perspective showing of the coated stent of FIG. 2 positioned over an ePTFE tube of FIG. 4.

The present invention provides a stent/graft composite endoluminal prostheses 22 shown in FIG. 5 including a stent 2 of the type shown in FIG. 1 secured to a tubular graft 16 of the type shown in FIG. 4. An improved method of forming such composite structure in accordance with the present invention includes providing a an adhesive bond between stent 2 and graft 16 by use of a polymeric coating 14 on stent 2 as shown in FIG. 2.

Figure 2:
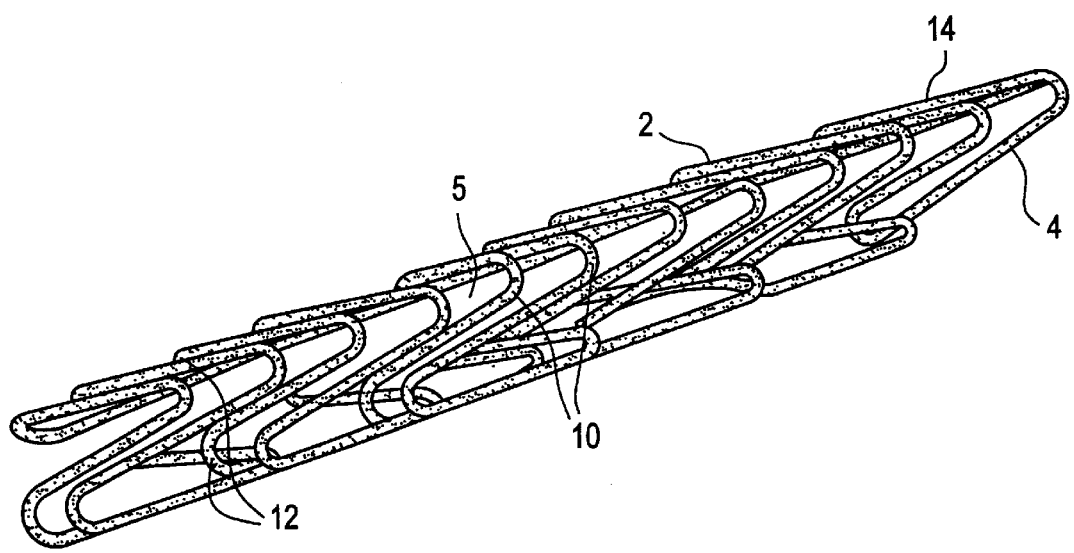
FIG. 2 is a perspective showing of a collapsed standard wave-like stent with a polymeric coating.

Referring specifically to FIGS. 1 and 2 of the drawings, one type of stent which may be included in the composite endoluminal prosthesis of the present invention is shown. Stent 2 is formed from an elongate wire 4 which is helically wound with a plurality of longitudinally spaced turns into an open tubular configuration. Stent 2 is an expandable tubular member which may be either of the balloon-expandable or self-expandable type. As previously discussed, one type of self-expanding stent may be formed of a shaped memory material such as nitinol. The elongate helically wound wire 4 forming stent 2 defines successive upper wave-like peaks 10 and lower wave-like peaks 12. Wire 4 is wound into a specific configuration where upper peaks 10 are placed adjacent to lower peaks 12 of the next adjacent winding.

In order to effectively form the composite endoluminal prosthesis of the present invention, stent 2 is coated with polymeric coating 14. Polymeric coating 14 is a biocompatible material, desirably PTFE. Polymeric coatings useful in the present invention include those biocompatible materials which are capable of adhering to PTFE grafts and desirably ePTFE grafts. Among those coatings contemplated are polytetrafluoroethylene (PTFE), expanded PTFE (ePTFE), polyurethane, fluorinated ethylene propylene (FEP), silicone, polyurethane-acrylate, silicone-acrylate, urethane-silicone, and the like. Combinations of these polymers may also be useful. Portions of the stent may also be coated with different polymers.

One particularly desirable form of polymer coating is one formed by polymeric particles or powder. PTFE powder coatings have been found to be especially useful in the present invention since these coatings bond well under heat and pressure to ePTFE tubular grafts. Other coatings are contemplated, however, and can include those which can flow into the porous structure of the graft or which are capable of bonding to PTFE or ePTFE.

The polymeric coating may be applied to stent 2 using a number of different techniques. Two preferred examples of application of coating 14 include spraying the stent with a spray of PTFE particles or dip coating the stent in a mixture containing PTFE particles. Powder coating generally refers to a variety of methods employing powdered plastics and resins which are used commercially to apply coatings to various articles. These methods include fluidized bed, electrostatic spray, electrostatic fluidized bed, plasma spray, and hot flocking, as well as combinations and variants of these methods.

In the electrostatic spray process, a coating powder is withdrawn from a reservoir in an air stream and electrostatically charged in the high voltage corona field of a spray gun. The charged particles are attracted to the grounded metal object to be coated and adhere to it by electrostatic attraction. The coated substrate is then placed in an oven and the coating is fused to form a substantially continuous film. The discrete PTFE particles form a connected path around the stent. The relatively high viscosity of the PTFE melt serves to effectuate a superior coating. If the powder is sprayed on a preheated article, the powder melts and fuses directly on the hot surface; further heating to fuse or cure the coating may be required, depending upon the type of coating powder.

Plasma coating is a method comprising establishing a hot temperature plasma in an inert gas such as nitrogen, and the coating powder is introduced at the periphery of the plasma. The particles melt and are propelled at high velocity to the substrate, where they form a film. In hot flocking techniques, powders are usually dispersed in air and sprayed or blown onto the preheated substrate, where they melt and form a coating. In a variant of this process, small parts are preheated and dropped into a bed of powder kept in a mobile state by vibration. In this method, the parts are completely coated with an unfused layer of powder on the surface.

Another method for coating the stent is to suspend stent 2 in the air, such as, on a hook, and spray the polymeric coating onto the stent according to the electrostatic spray method mentioned above. An advantage of applying the powder coating in this manner, is that it would sufficiently coat the stent in its entirety, and thus provide improved adhesion at its mating surface to the graft.

Figure 3:
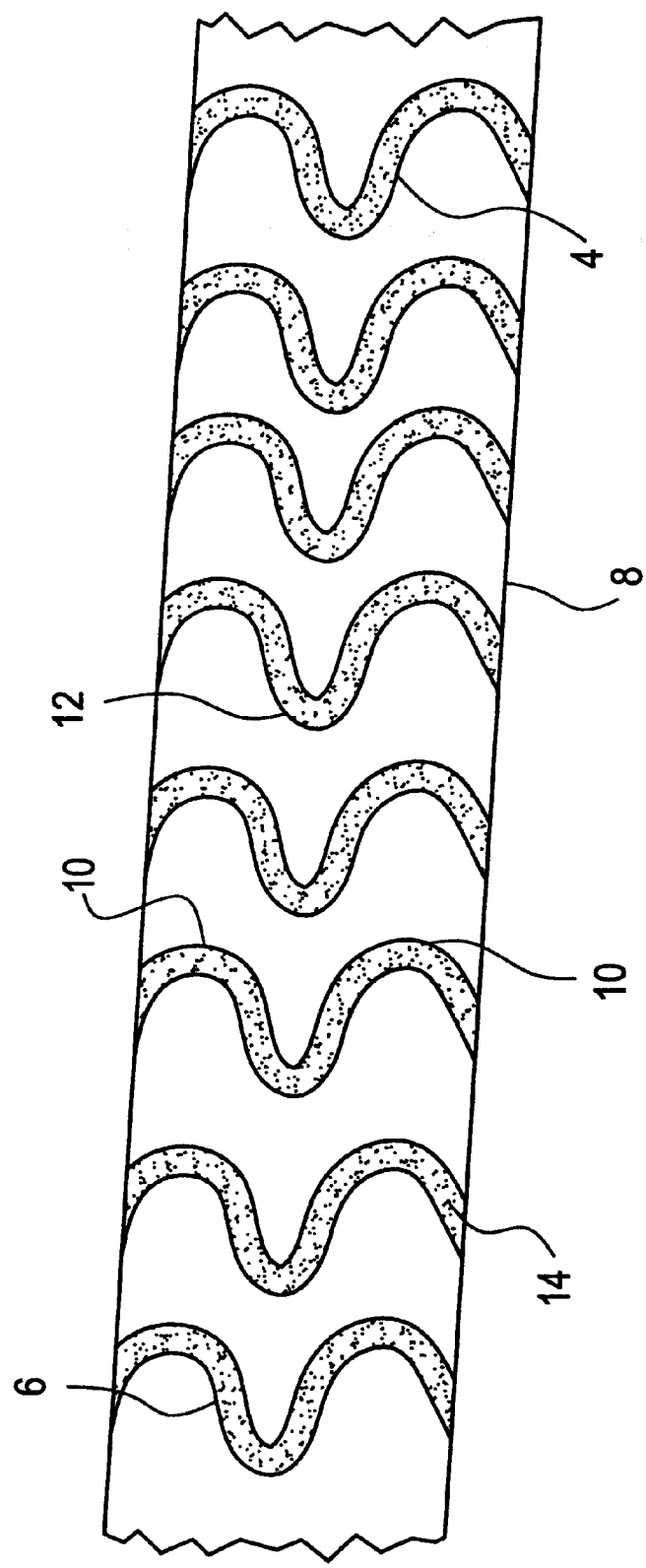
FIG. 3 is a perspective showing of the coated stent of FIG. 2 expanded over a mandrel.

Referring to FIG. 3, a desirable method for applying coating 14 to stent 6 is shown. Stent 6 is shown in an expanded state, and may be supported on a mandrel 8. Mandrel 8 is a rod-like stainless steel member of diameter approximately equal to that of the expanded stent. Once positioned on mandrel 8, stent 6 is polymeric coated with coating 14. PTFE polymeric coating 14 desirably forms a thin film on the wire. The thickness of the PTFE coating generally ranges from about 1 to about 100 microns. Coated stent 6 can then be removed from mandrel 8 tubular graft 16 to form the composite structure, or left on mandrel 8 and tubular graft 16 placed thereover.

Assembly of the stent/graft prosthesis includes the steps to positioning the graft either on the outside or the inside of the stent and using the combination of heat and pressure sufficient to adheringly assemble the components together. Tubular graft material can be used on both the interior and exterior of the tubular stent, as well. The graft may be a continuous tube, or may be formed with discontinuous sections. Tubular wrapping in a helical pattern is also contemplated.

As shown in FIG. 2, the entire stent may be coated with polymeric coating 14. It is further contemplated, however, that the stent may be partially coated with the polymeric coating at selected regions (FIG. 6) for purposes which will be described in detail hereinbelow.

Referring now to FIG. 4, graft 16 is a tubular structure of conventional construction formed of ePTFE. Graft 16 may be extruded as a tube or may be formed from an extruded sheet which is subsequently formed into a tubular structure. Textile or fabric constructions formed of PTFE or ePTFE yarns, filaments or mesh may also be employed.

FIG. 5 shows a perspective of a composite endoluminal prosthesis 22 comprised of stent 6 with polymeric coating 14, which circumferentially encloses ePTFE graft 16. The PTFE polymeric coating provides a bonding interface between the stent wire and the graft 16. The coated stent 6 is bonded to graft 16 by sintering the composite structure over a suitable mandrel such as, for example, mandrel 8 (FIG. 3).

It is further contemplated that this bonding interface may be enhanced by first coating the stent with the PTFE polymeric coating, then less than fully sintering the PTFE coating on stent 6. By sintering stent 6 less than fully, i.e. only partially sintering, the stent can then be placed on the ePTFE tubular graft 16 and sintered again over the mandrel. The subsequent sintering of the partially sintered coating 14 on graft 16 serves to increase bonded interface between graft 16 and stent 6.

Figure 6:
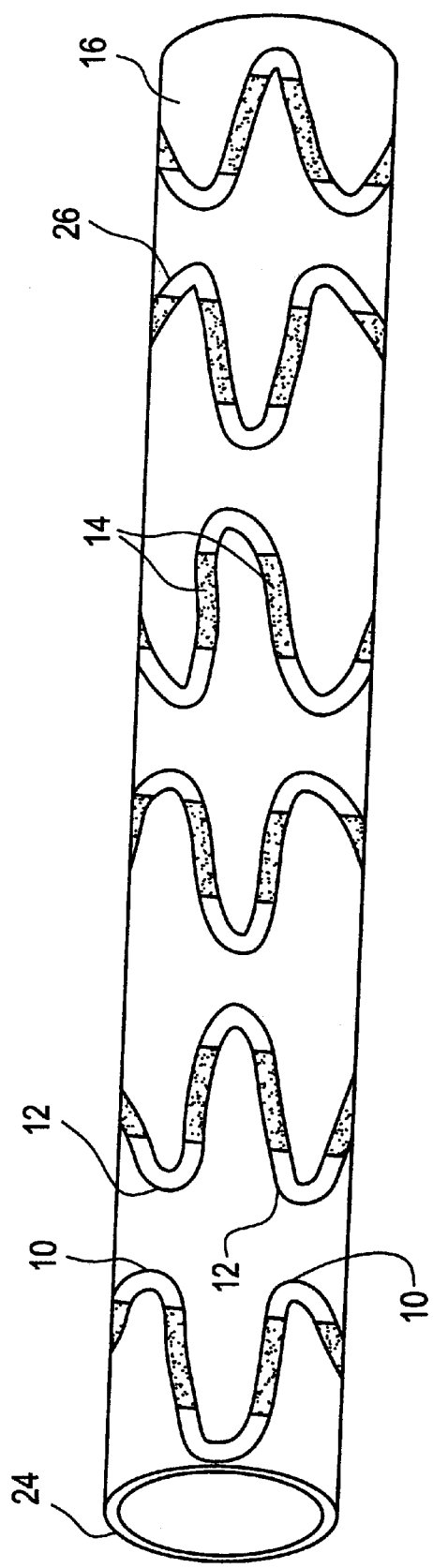
FIG. 6 is a perspective showing of a further embodiment of the present invention employing a stent with a partial polymeric coating over a PTFE tube.

Referring to FIG. 6, a further embodiment of the present invention is shown. A composite intraluminal prosthesis 24 is shown including an ePTFE graft 16, circumferentially enclosed by a partially coated polymeric stent 26. The composite structure may be assembled as described above. In this embodiment of the present invention, stent 26 is partially coated with PTFE coating 14 at areas intermediate of the undulations in the stent. By partially coating stent 6, the upper and lower wave-like peaks 10, and 12 respectively, are subsequently left exteriorly exposed without PTFE coating. This embodiment provides the composite graft with increased flexibility as the unexposed peaks do not readily bond to the graft. This provides multiple points of flexure throughout the length of the composite prosthesis 22.

Figure 7:
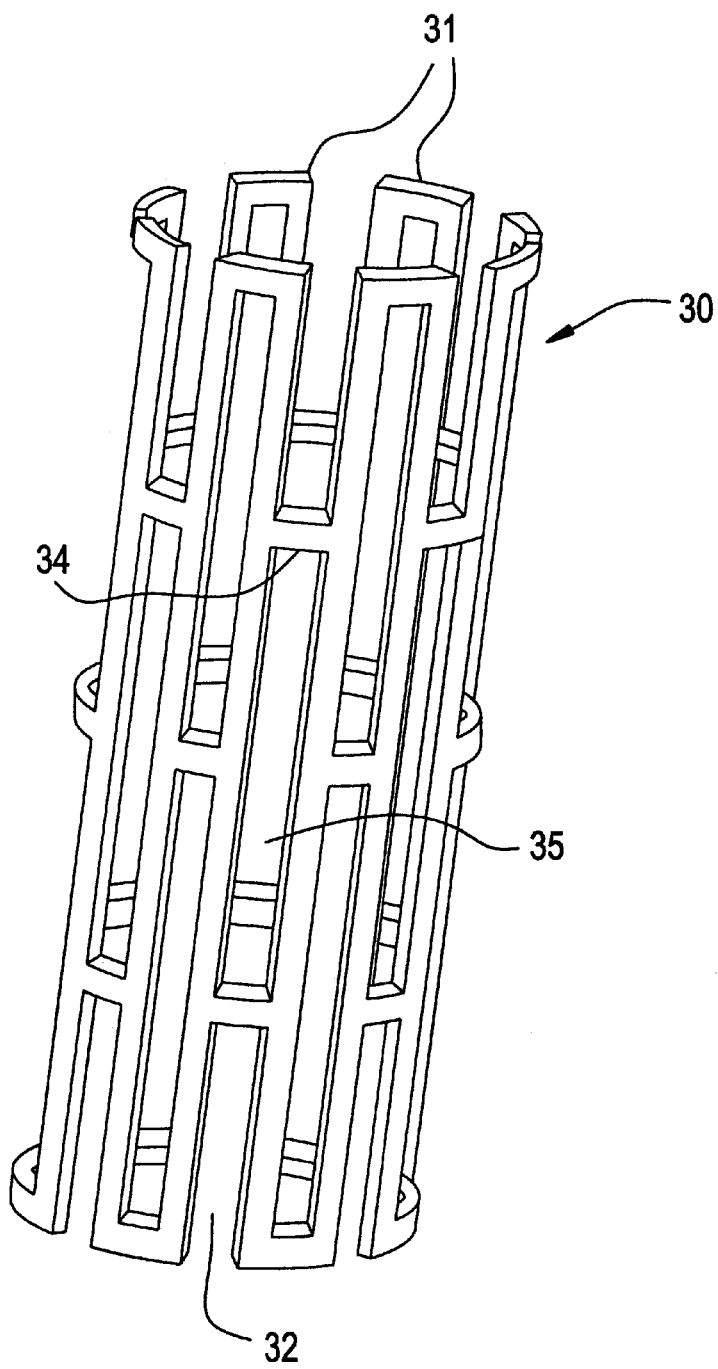
FIG. 7 is a perspective showing a different type of a stent which may be used in the present invention.

The particular wire stent 6 of FIGS. 1—6 is shown as merely one example. Other stent configurations, as discussed above, may be employed. For example, FIG. 7 shows another stent configuration which may be used in the present invention is shown. Stent 30 may be the type more fully described in U.S. Pat. No. 4,733,665, and is herein incorporated by reference. Stent 30 is an expandable and deformable tubular structure including a plurality of longitudinally extending parallel struts 31 connected to one another by transverse tabs 34. The struts 31 and tabs 34 define slots 32 which define open spaces 35 through the tube. This stent construction not only ensures patency and flexibility with the slotted configuration, but the configuration of slots and tabs would allow for a partially covered polymeric coating with increased flexibility as shown in FIG. 6. Stent 30 fully or partially coated as described above is subsequently bound to a tubular graft 16 (FIG. 4) in a manner described above to form a composite endoluminal prosthesis 22.

Various modifications and changes may be made without departing from the spirit and intent of the invention and all such changes are intended to be included in the following claims.

What is claimed is:

1. A method of forming a prosthetic device comprising the steps of:

providing an ePTFE tubular structure;

providing a tubular stent;

coating said stent with a flowable polymeric coating;

partially sintering said polymeric coating on said tubular stent;

placing said tubular stent circumferentially surrounding said ePTFE tubular structure; and affixing said tubular structure to said stent by fully sintering said stent to said tubular structure.

2. A method according to claim 1 wherein said polymeric coating is polytetrafluoroethylene.

3. A method according to claim 2 wherein the polymeric coating is powdered particulate polytetrafluoroethylene.

4. A method according to claim 1 wherein said polymeric coating covers the entire stent.

5. A method according to claim 1 wherein said stent is a tubular diametrically deformable stent formed from an elongate wire helically wound with a plurality of longitudinally spaced turns into an open tubular configuration, each of said turns including successive upper and lower wave-like peaks.

6. A method according to claim 5 wherein the selective peaks of said upper and lower wave-like peaks of said stent are exposed exteriorly of said polymeric coating.

7. A method according to claim 1 wherein said flowable polymeric coating covers said tubular stent entirely.

8. A method according to claim 1 wherein said flowable polymeric coating covers said tubular stent partially.

9. A method according to claim 8 wherein said tubular stent is affixed to said tubular structure at selected locations.

10. A method according to claim 6 wherein the tubular stent is affixed to said tubular structure at locations intermediate said upper and lower wave-like peaks.

11. A method according to claim 1 wherein said polymeric coating is selected from the group consisting of polytetrafluoroethylene, polyurethane, fluorinated ethylenepropylene, silicone, silicone-acrylate, urethane-acrylate, urethane-silicone, and combinations thereof.

12. A method according to claim 1 wherein said polymeric tubular structure is formed of polytetrafluoroethylene.

13. A method according to claim 12 wherein said tubular structure may be formed by extruding a tube of polytetrafluoroethylene.

14. A method according to claim 12 wherein said tubular structure is a textile graft formed by a method chosen from the group consisting of: braiding, weaving, and knitting of textile strands.

* * * * *

UNITED STATES PATENT AND TRADEMARK OFFICE
CERTIFICATE OF CORRECTION

PATENT NO. : 6,733,524 B2
DATED : May 11, 2004
INVENTOR(S) : D. Tseng et al.

It is certified that error appears in the above-identified patent and that said Letters Patent is hereby corrected as shown below:

Column 3,
Line 7, should read -- ...includes providing a tubular stent,... --.

Column 4,
Line 6, should read -- ...includes providing an adhesive bond... --.

Signed and Sealed this

Twentieth Day of July, 2004

JON W. DUDAS
*Acting Director of the United States Patent and Trademark Office*